United States Patent [19]

Sting et al.

[11] Patent Number: 4,878,747
[45] Date of Patent: Nov. 7, 1989

[54] APERTURE IMAGE BEAM SPLITTER

[75] Inventors: Donald W. Sting, New Canaan; Roger G. Messerschmidt, Westport, both of Conn.

[73] Assignee: Spectra-Tech, Inc., Stamford, Conn.

[21] Appl. No.: 302,112

[22] Filed: Jan. 24, 1989

Related U.S. Application Data

[63] Continuation of Ser. No. 13,584, Feb. 11, 1987, abandoned, which is a continuation-in-part of Ser. No. 707,231, Mar. 1, 1985, Pat. No. 4,653,880.

[51] Int. Cl.$^4$ .............................................. G02B 21/06
[52] U.S. Cl. ..................................... 350/511; 350/172; 350/527
[58] Field of Search ............... 350/171, 172, 511, 523, 350/527, 561, 562, 566, 571, 572, 573, 600, 601

[56] References Cited

U.S. PATENT DOCUMENTS

| 3,411,852 | 11/1968 | Marinozzi, Jr. | 350/622 |
| 3,585,281 | 6/1971 | Jordan | 350/171 |
| 3,968,362 | 7/1976 | Mocker | 250/216 |
| 4,479,700 | 10/1984 | Abe | 350/523 |
| 4,531,054 | 7/1985 | Suzuki | 350/172 |
| 4,594,509 | 6/1986 | Simon | 250/338 |
| 4,653,880 | 3/1987 | Sting | 350/620 |

FOREIGN PATENT DOCUMENTS

| 2722787 | 11/1978 | Fed. Rep. of Germany | 350/172 |
| 359783 | 1/1962 | Switzerland . | |

OTHER PUBLICATIONS

Analect, "Micro-FTIR Spectrometers and FTIR Microscopes" Advertising Brochure From Analect Instruments, Irvine Calif.

Primary Examiner—Bruce Y. Arnold
Assistant Examiner—Martin Lerner
Attorney, Agent, or Firm—Calfee, Halter & Griswold

[57] ABSTRACT

An improved aperture beam splitter comprises an intercepting mirror positioned at an aperture image plane that is remote from any focus so as to deflect one half of the energy in a beam of incident radiant energy. the aperture image plane corresponds to an aperture stop and one half of an incident beam of radiant energy is lost at the aperture image plane. The remaining energy supplies the input to an optical system. The radiant energy from the output of the optical system reaches an image plane corresponding to the aperture image plane. Preferably, the optical paths of the incident and returning radiant energy are sufficiently coincident in space that the aperture image plane returns to the intercepting mirror. If the optical system forms the radiant energy into an odd number of foci, the image formed at the aperture image plane experiences a mirror symmetry reversal. The energy that was retained in the optical system during the first pass through the aperture image plane fills the other half of the aperture image plane so that the radiant energy returning through the optical system can be separated in space from the incident radiant energy without additional loss of energy or loss of image information gained from an intervening focus.

8 Claims, 1 Drawing Sheet

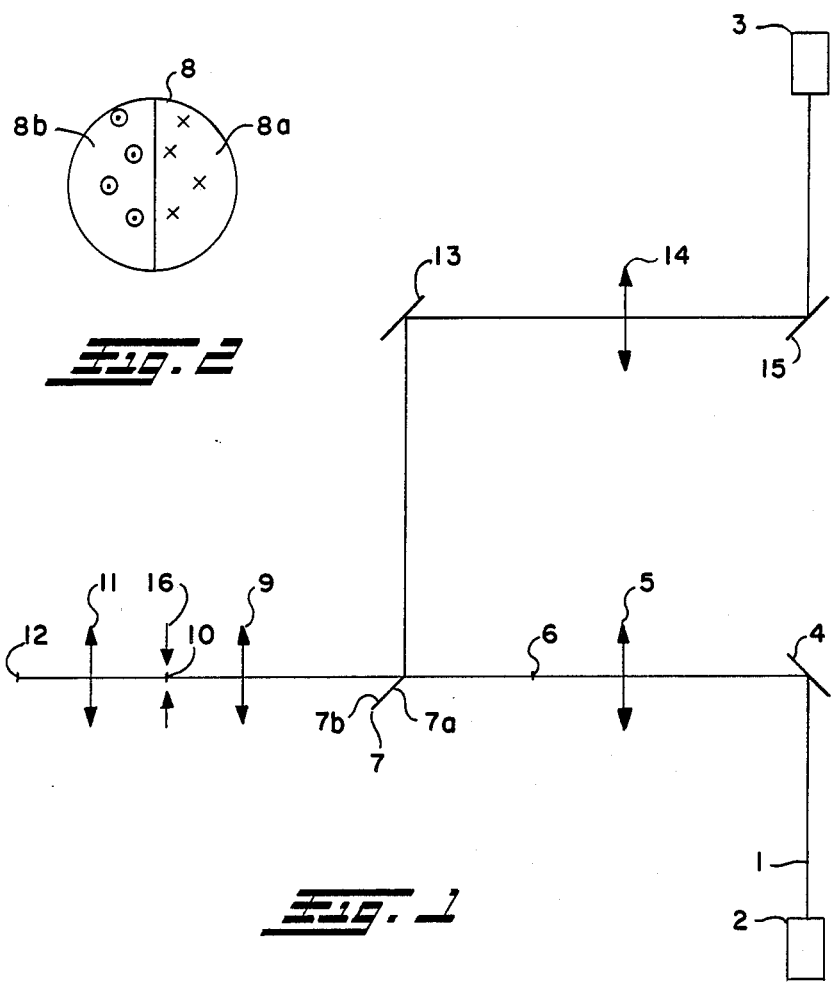

APERTURE IMAGE BEAM SPLITTER

RELATED APPLICATIONS

The present application is a continuation of co-pending application Ser. No. 013,584 now abandoned filed on Feb. 11, 1987, which is a continuation-in-part of copending U.S. patent application Ser. No. 707,231, now U.S. Pat. No. 4,653,880, titled Reflective Beam Splitting Objective, filed Mar. 1, 1985, assigned to the assignee of the present application, incorporated herein by reference. Application Ser. No. 829,085, filed Feb. 13, 1986, assigned to the present assignee, discloses another type of aperture beam splitter. application Ser. No. 015,315, filed Feb. 17, 1987, assigned to the present assignee, discloses and claims a microscope that, inter alia, masks incident and reflected radiant energy at the same remote image plane.

BACKGROUND OF THE INVENTION

1. Field of the Invention

The present invention relates to the general field of microscopy and particularly the field of fast Fourier-infrared (FT-IR) microspectrophotometry.

2. Description of Related Art

Copending U.S. patent application Ser. No. 707,231, now U.S. Pat. No. 4,653,880, title Reflective Beam Splitting Objective, discloses an aperture beam splitter formed entirely with mirror optics. The mirror optics can focus radiant energy having greatly differing wavelengths such as from the visible light region to the infrared. The beam splitter forms an integral unit with the imaging objective of the microscope. In the preferred embodiment, an intercepting mirror is positioned close to the secondary mirror of a Cassegrain reflective objective so as to divide in half the reflective surface of the secondary mirror. The intercepting mirror reflects half of a beam of incident radiant energy to the secondary so that energy from half of the aperture of the primary mirror forms an image at an image sample plane. The other half of the primary mirror collects the radiant energy from the surface of the sample. The arrangement of mirrors enables the reflective beam splitting objective to obtain a 50% throughput efficiency. Little if any of the image information about the sample is lost and the quality of the image is adequate for FT-IR microspectrophotometry. The reflective beam splitting objective, unlike conventional aperture beam splitters, eliminates the complexity and expense associated with collimating optics. Rather than collimating the radiant energy, the reflecting beam splitting objective receives radiant energy that is either converging or diverging.

The foregoing aperture beam splitter has several disadvantages. The intercepting mirror must be positioned in a confined space within the focusing objective. The relatively small physical dimensions of a microscope objective severely limit the physical size of the intercepting mirror. Further, the confined physical space within the objective makes aligning the intercepting mirror most critical. The difficulty associated with obtaining and maintaining the alignment increases the cost of the objective beam splitter. The integral structure of the reflective beam splitting objective requires that each microscope objective contain a properly aligned intercepting mirror. Commercially available reflecting objectives therefore cannot be used without expensive modification.

SUMMARY OF THE INVENTION

The present invention relates to an improved aperture beam splitter. An intercepting mirror is positioned at an aperture image plane that is remote from any sample image. Preferably, the aperture image plane corresponds to an aperture stop. Half of the beam of radiant energy is lost at the aperture image plane. The remaining energy supplies the input to an optical system. The output of the optical system eventually returns to an image plane corresponding to the aperture imaging plane. Preferably, the optical paths of the incident and returning radiant energy are sufficiently coincident in space that the aperture image plane returns to the intercepting mirror. If the optical system focuses the radiant energy an odd number of times, the aperture image experiences a mirror symmetry reversal. The energy that was retained in the optical system during the first pass through the aperture image plane fills the other half of the aperture image plane. Thus, the intercepting mirror can separate the beam of incident radiant energy from the beam of returning radiant energy without additional loss of energy or loss of image information gained from an intervening focus.

The improved aperture beam splitter according to the present invention retains the advantages of the above identified reflective beam splitting objective without requiring a critical positioning of the intercepting mirror. The greater tolerance reduces the cost of manufacturing the beam splitter and simplifies the task of obtaining and maintaining a proper optical alignment. Further, the aperture image beam splitter works with all commercially available condensers and objectives and thus eliminates the time and expense associated with inserting and aligning an intercepting mirror in each microscope objective.

BRIEF DESCRIPTION OF THE DRAWING

FIG. 1 is a schematic illustration of an aperture image beam splitter embodying the present invention; and FIG. 2 shows the distribution and direction of propagation of the radiant energy forming the aperture image at the intercepting mirror in FIG. 1.

DETAILED DESCRIPTION OF THE PREFERRED EMBODIMENT

FIG. 1 is a schematic illustration of an aperture image beam splitter embodying the present invention. A beam of radiant energy 1 emanates from a source 2 to a detector system 3. The source 2 and detector system 3 comprise parts of a fourier transform - infrared (FT-IR) spectrophotometer, many examples of which are well known in the art. Transfer optics comprising mirror 4 reflect the radiant energy out of the sample compartment or "shoe box" of the spectrophotometer, not shown in FIG. 1. Additional transfer optics, comprising one or more mirrors, lenses, or combinations thereof and symbolically illustrated by double arrow 5, focus the radiant energy at first sample image 6. Half of the diverging beam of incident energy from first sample image 6 fills surface 7a on intercepting mirror 7. Surface 7a discards the energy from the first sample image plane 6 by reflecting it to one side. The other half of the beam of incident energy passes by intercepting mirror 7.

Intercepting mirror 7 is positioned at what is defined for the purpose of the present description as an aperture image plane 8. FIG. 2 shows the distribution of intercepting the radiant energy at the aperture image plane.

The direction of the radiant energy is shown using conventional arrow head and arrow tail notation. The beam of incident radiant energy that passes by intercepting mirror 7 fills input region 8a. The direction of propagation direction into the paper in FIG. 2 is indicated by the crosses symbolizing tails of the vector arrows.

An optical system, symbolically indicated by double arrow 9 in FIG. 1, focuses the incident beam of radiant energy at a second sample image 10. The optical system may also include an additional set of optics symbolically indicated by double arrow 11 to image the radiant energy at sample 12. The imaging optics indicated by double arrows 9 and 11 may comprise one or more mirrors, lenses or combinations thereof. Mirror optics exhibit no chromatic aberration and are therefore preferred. The optical system formed by optics 9 and 11 preferably comprise a microscope for FT-IR microspectrophotometry.

As shown in FIG. 1, optics 11 image the radiant energy reflected from a sample 12 to the second sample image 10. The radiant energy from the sample reflected through the optical system forms an aperture image 8b at the plane of mirror 7. The returning radiant energy is indicated as output 8b in FIG. 2 by the dots and circles which symbolize the heads of arrows. The aperture images 8a and 8b are mirror images whenever the radiant energy is focused at an odd number of sample image planes before returning to aperture plane 8. This result, however, requires that the image information carried by the radiant energy is not scrambled or otherwise destroyed. The radiant energy in the returning beam from the sample fills the area of the aperture image plane from which energy was originally removed at surface 7a at intercepting mirror 7. A reflecting surface 7b, provided on the back side of mirror 7, reflects the beam of returning radiant energy from the aperture image to transfer optics comprising mirror 13. Additional transfer optics, comprising one or more mirrors, lenses or combinations thereof and symbolically represented by double arrow 14, modify the divergence of the returning beam of radiant energy so that it is reflected by mirror 15 to a focus at detector system 3.

Intercepting mirror 7 must be positioned at a location that is remote from any sample image plane of the optical system, such as first sample image 6. Reflective surface 7a preferably corresponds to an aperture stop for the beam of incident radiant energy. The aperture image contains radiant energy from all the points of first sample image 6 because intercepting mirror 7 only reduces the effective aperture of the system. The image information gained at any of the sample images is therefore not vignetted by the intercepting mirror. However, the intercepting mirror does reduce the brightness of each subsequent image. The numerical aperture, and hence the effective resolution of any subsequent focusing optics, is also reduced so long as the radiant energy continues to transmit the image of the intercepting mirror at the aperture image plane.

It is preferred that surface 7a of mirror 7 intercept exactly one half of the beam of radiant energy as shown in FIG. 2. Intercepting more than one half of the radiant energy with mirror 7 is inefficient because radiant energy is wasted and the effective aperture is reduced. Conversely, intercepting less than one half of the radiant energy is also inefficient because the extra radiant energy cannot be directed to the detector on the return, thus reducing the effective numerical aperture of the optical system.

An intermediate sample image, such as second sample image 10, may be masked with a variable aperture diaphragm or set of razor blades to form an arbitrary geometric shape. The image of the mask is projected onto all other sample images in the optical system. The ability to mask an intermediate sample image and project the image of that remote sample image onto a sample is considered a major utility of the present invention in the field of FT-IR microspectrophotometry.

Numerous modifications may be made to the optical scene shown in FIG. 1. For example, the reflectance mode microscope system shown in FIG. 1 may be replaced by a transmissive mode microscope system. The intercepting mirror may reflect the beam of incident radiant energy into the optical system rather than reflect the beam of returning radiant energy to the detector as done in the embodiment shown in FIG. 1. The intercepting mirror(s) may be positioned at any place in the optical path that is remote from a focus and preferably at an aperture stop. The intercepting mirror has no maximum size and may be positioned within comparatively wide tolerances. The wide tolerances greatly simplifies the process of aligning the intercepting mirror and reduce manufacturing costs while also maintaining the quality of the optical system. Additional transfer optics may be added to the optical system shown in FIG. 1 to accomplish any number of objectives or to simplify any other mechanical alignments.

The principles, preferred embodiments and modes of operation of the present invention have been described in the foregoing specification. The invention which is intended to be protected herein should not, however, be construed as limited to the particular forms described herein as these are to be regarded as illustrative rather than restrictive. Variations and changes may be made by those skilled in the art without departing from the spirit of the invention. Accordingly, the foregoing detailed description should be considered exemplary in nature and not as limiting to the scope and spirit of the invention set forth in the appended claims.

What is claimed is:

1. An optics system for spectroscopic analysis having an aperture image beam splitter comprising:
   a radiant energy source;
   a sample;
   first optics means to direct an incident radiant energy beam from the source to the sample, the first optics means being operative to focus the incident radiant energy at least at first and second sample images and at the sample;
   means to discard part of the incident radiant energy from the system while transmitting the rest of the incident radiant energy through the first optics means to the sample; and
   an intercepting mirror positioned between the first and second sample images at an aperture image plane;
   the first optics means directing some specularly reflected radiant energy from the sample back through the second sample image to the intercepting mirror, the intercepting mirror being operative to reflect the specularly reflected energy through second optics means to a detector.

2. An optics system for spectroscopic analysis as set forth in claim 1 wherein the aperture image plane constitutes an aperture stop for the optics system.

3. An optics system for spectroscopic analysis as set forth in claim 1 wherein said first optics means is operative to form an odd number of sample images between the intercepting mirror and the sample.

4. An optics system for spectroscopic analysis as set forth in claim 1 further including an adjustable mask at the second sample image.

5. An optics system for spectroscopic analysis as set forth in claim 1 wherein the intercepting mirror has a first mirrored side reflecting the specularly reflected energy from the sample to the second optics means and a second side constituting the means to discard, the intercepting mirror being positioned and sized to discard approximately one-half of the incident radiant energy beam.

6. A method for spectroscopic analysis of a sample comprising the steps of:
   directing incident radiant energy from a source to a sample;
   focusing the incident radiant energy at least at first and second sample images and at the sample;
   discarding part of the incident radiant energy from the system while transmitting the rest of the incident radiant energy to the sample;
   directing specularly reflected energy from the sample back toward the second and first sample images;
   intercepting the specularly reflected energy at an aperture image plane and
   directing the intercepted specularly reflected energy to a detector.

7. An optics system for spectroscopic analysis comprising:
   a radiant energy source;
   a sample;
   optics means to direct an incident radiant energy beam from the source to the sample, the optics being operative to focus the incident radiant energy beam at first and second sample image planes and at the sample;
   the optics means including an aperture image beam splitter positioned between the first and second sample image planes;
   the aperture image beam splitter being operative to discard part of the incident radiant energy beam from the system while transmitting the rest of the incident radiant energy beam through the second sample image plane to the sample and being further operative to transmit radiant energy reflected from the sample back through the second sample image plane to a detector.

8. The optics system of claim 7 wherein the aperture image beam splitter is semi-circular to discard one-half of the incident radiant energy beam while transmitting the other half of the incident radiant energy beam.

* * * * *